US00PP09434P

United States Patent [19]

Frazer

[11] Patent Number: Plant 9,434

[45] Date of Patent: Jan. 16, 1996

[54] DIEFFENBACHIA PLANT NAMED TROPIC DAWN

[75] Inventor: Edwin J. Frazer, Kenmore, Australia

[73] Assignee: Twyford International Inc., Sebring, Fla.

[21] Appl. No.: 374,860

[22] Filed: Jan. 19, 1995

[51] Int. Cl.[6] ..... A01H 5/00

[52] U.S. Cl. ..... Plt./88.2

[58] Field of Search ..... Plt./88.2

[56] References Cited

U.S. PATENT DOCUMENTS

P.P. 6,858 6/1989 Frazer ..... Plt./88.2

*Primary Examiner*—James R. Feyrer
*Attorney, Agent, or Firm*—Foley & Lardner

[57] ABSTRACT

A Dieffenbachia plant named Tropic Dawn characterized by its striking white markings, very dark green shiny foliage and durability in interiorscapes.

1 Drawing Sheet

The present invention comprises a new and distinct cultivar of Dieffenbachia, botanically known as *Dieffenbachia hybrida* and referred to by the cultivar name Tropic Dawn.

The new cultivar is a product of a planned breeding program carried out by the inventor Edwin J. Frazer in Brisbane, Australia. The new cultivar is a product of a cross made between the following:

Pollen parnet: Missouri Botanical Garden Acquisition No. 37949D MBG.

Seed parent: Hybrid No. 83138, derived from a cross between Wilson's Delight × Exotica.

The cultivar was discovered from the progeny of the stated cross by Edwin J. Frazer in Brisbane, Australia. Asexual propagation by tissue culture by the inventor in Brisbane, Australia increased the number of plants for evaluation and has demonstrated the stability of the combination of characteristics of Tropic Dawn from generation to generation.

The following observations, measurements and values describe plants grown in Apopka, Fla. under greenhouse conditions which closely approximate those generally used in horticultural practice.

The following traits have been repeatedly observed to be characteristics which in combination distinguish Tropic Dawn from other Dieffenbachia of the same general type, for example, the well-known cultivar Hilo, disclosed in U.S. Plant Pat. No. 6,858 and to which comparative reference is made.

1. The leaves of Tropic Dawn are broad, oblong, and thick when compared to those of Hilo.

2. The leaves are considerably darker green and very glossy when compared to those of Hilo.

3. The leaves have more prominent white marking than those of Hilo.

4. The plant resists damage common in shipping, and is notably durable in interiorscape growing conditions.

All color references are measured against The Royal Horticultural Society Colour Chart. Colors are approximate as color depends on horticultural practices such as light level and fertilization rate, among others, without, however any variance in genotype.

The color photographic drawing comprises a top perspective view of a plant of Tropic Dawn in a 21 cm pot approximately 40 weeks after planting a 12-week-old liner obtained by tissue culture and grown under appropriate growing conditions. Colors are as accurate as possible with color illustrations of this type.

Origin: Seedling selected from a cross between Missouri Botanical Garden Acquisition No. 37949D MBG (pollen parent) and Hybrid No. 83138 (seed parent).

Classification: *Dieffenbachia hybrida,* cv., Tropic Dawn.

Propagation: Asexual propagation either by tissue culture or division.

Plant: In a 21 cm pot for a plant grown from a 12-week-old liner after 40 weeks under appropriate growing conditions, Tropic Dawn reaches a height of approximately 33 cm from the soil surface to the junction of the petioles of the last two (2) unrolled leaves, and a width of approximately 50 cm to 58 cm.

Stem:

*Growth pattern.*—The stem is erect in growth and approximately 2.6 cm in diameter five (5) cm above the soil surface. Internode distance is approximately 1.5 cm to 2.2 cm three (3) cm above the soil.

*Color.*—The stem is sparsely striped and mottled with coarse lines of green and light greenish white similar to the petiole colors.

Petiole: The following information is based on the 4th expanded leaf from the apex.

*Growth pattern.*—The petiole has fleshy edges, referred to as wings, extending from the midrib. The wings are approximately 13 mm to 16 mm wide one-half (½) the distance from the petiole base to the wing apex, and extend from the base of the petiole to within approximately 3 mm to 5 mm of the base of the leaf. The apex of the wings is emarginate. The petiole follows the stem axis but diverges from the axis approximately 8.5 cm from the leaf base, forming a horizontal distance from the edge of the stem to the leaf base of approximately 2.5 cm.

*Dimensions.*—The petiole is straight from its base to the base of the leaf. The petiole is approximately 9 mm in diameter one-half the distance between the top of the wing and the base of the leaf, and is approximately 18 cm to 19.2 cm in length from its base to the base of the leaf.

*Color.*—The petiole wings are darker and greener than, but closest to 137A, finely mottled with 145 C-D. The midrib of the petiole is 145 C-D.

Leaf:

*Growth pattern.*—The leaf is oblong with a cuspidate apex and an obtuse base. The margin is entire. The leaf is asymmetric with the side of the leaf unrolling first having less surface area than the side unrolling last. The leaf is oriented parallel to the stem axis at the time of full unrolling, changing to approximately 60 degrees above perpendicular to the stem axis as more leaves unroll above it. The midrib is straight over the length of the leaf. The leaf blade is flat from the midrib to the margin, drooping slightly near the edge.

*Dimensions.*—For the pot size and growing time indicated, the largest leaf is approximately 32.5 cm to 34.5 cm long and approximately 17.2 cm to 18.7 cm wide. An average sized leaf is approximately 25.4 cm to 27.5 cm long and approximately 16 cm to 17.3 cm wide. The leaf is moderately thick.

*Midrib.*—The midrib is thick and prominent.

*Primary veins.*—The primary veins are sunken into the upper surface and protrude from the underside.

*Color and pattern.*—The upper surface of both the mature, older leaf and the newly opened leaf is very dark green with contrasting white midribs and primary veins. The upper surface of the leaf has a midrib color greener than but closest to 155A becoming 137A near the base of the leaf, and a leaf blade color darker and greener than, but closest to 139A. The midrib and primary veins on the lower surface of the leaf are 150D in color. The lower surface leaf blade color is 147B.

*Axillary Breaks.*—There are approximately 2 to 5 axillary breaks with at least one leaf expanded. Leaves show color by the first leaf and will have true color and pattern by the second leaf.

*Inflorescence.*—Typical of Dieffenbachia and does not have commercial significance.

Roots: Thick white roots with fine laterals.

General observations: Tropic Dawn is similar in leaf pattern to Hilo, but has very dark green, shiny oblong leaves. The plants are very well adapted to interiorscape conditions and resist shipping related damage. These combined characteristics make Tropic Dawn a unique new cultivar.

It is claimed:

1. A new and distinct cultivar of Dieffenbachia plant named Tropic Dawn, as illustrated and described.

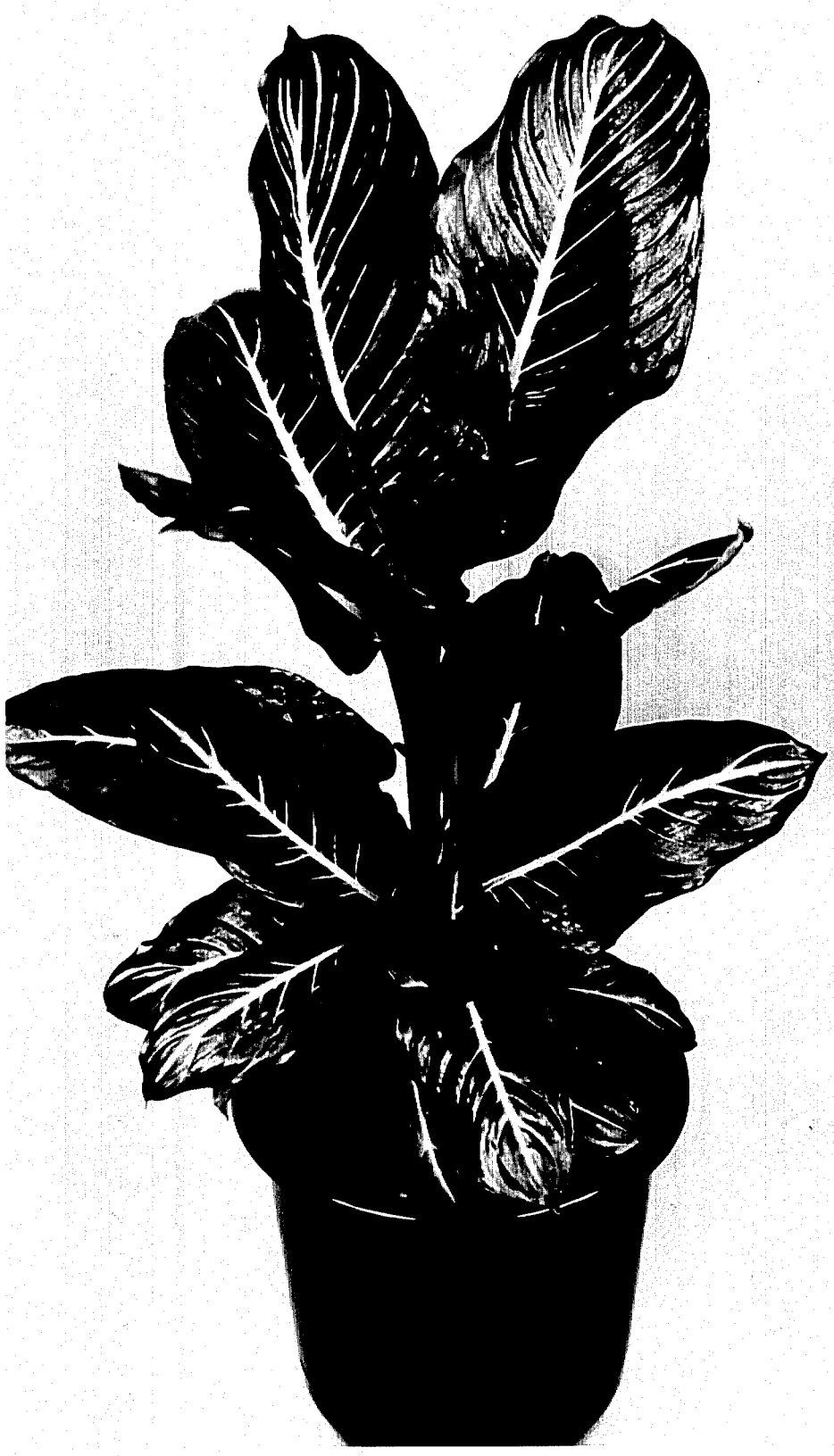

* * * * *